(12) United States Patent
Wang et al.

(10) Patent No.: US 9,619,620 B2
(45) Date of Patent: Apr. 11, 2017

(54) HEALTH MONITORING SYSTEM AND DATA COLLECTION METHOD THEREOF

(71) Applicant: BOE TECHNOLOGY GROUP CO., LTD., Beijing (CN)

(72) Inventors: Hong Wang, Beijing (CN); Yanshun Chen, Beijing (CN); Yaohui Li, Beijing (CN); Qiushi Xu, Beijing (CN)

(73) Assignee: BOE TECHNOLOGY GROUP CO., LTD., Beijing (CN)

( * ) Notice: Subject to any disclaimer, the term of this patent is extended or adjusted under 35 U.S.C. 154(b) by 242 days.

(21) Appl. No.: 14/436,294

(22) PCT Filed: Sep. 1, 2014

(86) PCT No.: PCT/CN2014/085656
§ 371 (c)(1),
(2) Date: Apr. 16, 2015

(87) PCT Pub. No.: WO2015/165188
PCT Pub. Date: Nov. 5, 2015

(65) Prior Publication Data
US 2016/0259903 A1 Sep. 8, 2016

(30) Foreign Application Priority Data
Apr. 28, 2014 (CN) .......................... 2014 1 0175481

(51) Int. Cl.
*G06F 19/00* (2011.01)
*A61B 5/00* (2006.01)

(52) U.S. Cl.
CPC ............ *G06F 19/3406* (2013.01); *A61B 5/00* (2013.01); *A61B 2560/0209* (2013.01)

(58) Field of Classification Search
CPC . A61B 5/00; A61B 2560/0209; A61B 5/0002; G06F 19/3406; G06F 19/3418; H04W 84/20
See application file for complete search history.

(56) References Cited

U.S. PATENT DOCUMENTS

2007/0015973 A1* 1/2007 Nanikashvili .......... A61B 5/002
600/300
2007/0282177 A1* 12/2007 Pilz ........................ A61B 5/411
600/301

(Continued)

FOREIGN PATENT DOCUMENTS

CN 101170943 A 4/2008
CN 101467878 A 7/2009

(Continued)

OTHER PUBLICATIONS

Korean Office Action dated Oct. 26, 2016 issued in corresponding Korean Application No. 10-2015-7012392.

(Continued)

*Primary Examiner* — An T Nguyen
(74) *Attorney, Agent, or Firm* — Nath, Goldberg & Meyer; Joshua B. Goldberg; Christopher Thomas

(57) ABSTRACT

The present invention discloses a health monitoring system and a data collection method of the health monitoring system. The health monitoring system includes an intelligent monitoring system and a micro-monitoring system, wherein the micro-monitoring system is configured to judge whether the intelligent monitoring system is completely started, and if it judges that the intelligent monitoring system is completely started, the micro-monitoring system transmits the human body data information collected by the collection device to the intelligent monitoring system; if it judges that the intelligent monitoring system is not completely started, the micro-monitoring system processes the human body data (Continued)

information collected by the collection device and transmits the processed human body data information to a display terminal. The health monitoring system can effectively solve the problem that the intelligent monitoring system fails to monitor the health indicators of a human body during a start process.

8 Claims, 2 Drawing Sheets

(56) References Cited

U.S. PATENT DOCUMENTS

2009/0240120 A1  9/2009  Mensinger et al.
2012/0161959 A1* 6/2012  Palmer ................ A61B 5/0002
                                              340/539.12

FOREIGN PATENT DOCUMENTS

| CN | 101632581 A | 1/2010 |
| CN | 101669821 A | 3/2010 |
| CN | 102512174 A | 6/2012 |
| CN | 103156575 A | 6/2013 |
| CN | 103239218 A | 8/2013 |
| CN | 103976710 A | 8/2014 |
| CN | 104027069 A | 9/2014 |
| WO | 2013/066642 A1 | 5/2013 |
| WO | 2014/027273 A1 | 2/2014 |

OTHER PUBLICATIONS

Chinese Office Action dated Feb. 27, 2015 issued in corresponding Chinese Application No. 201410175481.X.

International Search Report dated Jan. 26, 2015 issued in corresponding International Application No. PCT/CN2014/085656 along with an English translation of the Written Opinion.

* cited by examiner

HEALTH MONITORING SYSTEM AND DATA COLLECTION METHOD THEREOF

This is a National Phase Application filed under 35 U.S.C. 371 as a national stage of PCT/CN2014/085656, filed Sep. 1, 2014, an application claiming the benefit of Chinese Application No. 201410175481.X, filed Apr. 28, 2014, the content of each of which is hereby incorporated by reference in its entirety.

FIELD OF THE INVENTION

The present invention relates to the field of health monitoring, and particularly to a health monitoring system and a data collection method thereof.

BACKGROUND OF THE INVENTION

With the improvement of living standards of people, corresponding medical healthcare service systems have been gradually improved, and meanwhile a health monitoring system with an intelligent operating system emerges as the right moment. Currently, the health monitoring system generally includes an intelligent monitoring system, which can independently process collected human body data information and transmit the processed human body data information to a display terminal for displaying, so that a monitored object can understand his/her health indicators to facilitate subsequent diagnosis and treatment.

However, since both the hardware (structure) and software (operating system) of the intelligent monitoring system are relatively complex, a long start time is needed when each time the system is started, resulting in that the monitored object cannot obtain the health indicators in real time.

SUMMARY OF THE INVENTION

The present invention provides a health monitoring system and a data collection method thereof, which can obtain the health indicators of a human body in real time.

To achieve the above-mentioned object, the present invention provides a health monitoring system, including an intelligent monitoring system and a micro-monitoring system, wherein the micro-monitoring system is connected with the intelligent monitoring system, and a collection device is connected to the micro-monitoring system;

the collection device is configured to collect human body data information; and the micro-monitoring system is configured to judge whether the intelligent monitoring system is completely started, and if it judges that the intelligent monitoring system is completely started, the micro-monitoring system transmits the human body data information collected by the collection device to the intelligent monitoring system; if it judges that the intelligent monitoring system is not completely started, the micro-monitoring system processes the human body data information collected by the collection device and transmits the processed human body data information to a display terminal.

Optionally, the micro-monitoring system includes a first detection module, a first transmission module and a second transmission module, the first detection module being connected with the first transmission module and the second transmission module, the first detection module is configured to detect whether the first detection module receives a complete startup signal sent by the intelligent monitoring system;

the first transmission module is configured to process the human body data information collected by the collection device and transmit the processed human body data information to the display terminal, when the first detection module detects that the first detection module does not receive the complete startup signal; and the second transmission module is configured to transmit the human body data information collected by the collection device to the intelligent monitoring system, when the first detection module detects that the first detection module receives the complete startup signal.

Optionally, the micro-monitoring system further includes a second detection module connected with the second transmission module;

the second detection module is configured to detect whether the second detection module receives a standby control signal sent by the intelligent monitoring system, after the second transmission module transmits the human body data information collected by the collection device to the intelligent monitoring system;

if the second detection module detects that the second detection module receives the standby control signal, the micro-monitoring system enters a standby state; and if the second detection module detects that the second detection module does not receive the standby control signal, the second transmission module continues to transmit the human body data information collected by the collection device to the intelligent monitoring system.

Optionally, the micro-monitoring system further includes a judging module connected with the first detection module and the first transmission module;

the judging module is configured to judge whether the collection device continues to collect the human body data information after the first transmission module sends the processed human body data information to the display terminal;

if the judging module judges that the collection device continues to collect the human body data information, the first detection module continues to detect whether it receives the complete startup signal sent by the intelligent monitoring system; and if the judging module judges that the collection device does not continue to collect the human body data information, the micro-monitoring system enters the standby state.

Optionally, the micro-monitoring system includes a single chip microcomputer, the single chip microcomputer being connected with the collection device through an I/O interface, and the single chip microcomputer being connected with the intelligent monitoring system through an IIC bus or an SPI bus.

To achieve the above-mentioned object, the present invention provides a data collection method of a health monitoring system, the health monitoring system including an intelligent monitoring system and a micro-monitoring system, the micro-monitoring system being connected with a collection device, and the method including the following steps:

judging, by the micro-monitoring system, whether the intelligent monitoring system is completely started;

transmitting, by the micro-monitoring system, human body data information collected by the collection device to the intelligent monitoring system if the judging indicates that the intelligent monitoring system is completely started; and processing, by the micro-monitoring system, the human body data information collected by the collection device and transmitting the processed human body data information to a display terminal if the judging indicates that the intelligent monitoring system is not completely started.

Optionally, the step of judging, by the micro-monitoring system, whether the intelligent monitoring system is completely started includes:

detecting whether the micro-monitoring system receives a complete startup signal sent by the intelligent monitoring system;

judging that the intelligent monitoring system is completely started if the detecting indicates that the micro-monitoring system receives the complete startup signal; and judging that the intelligent monitoring system is not completely started if the detecting indicates that the micro-monitoring system does not receive the complete startup signal.

Optionally, after the step of transmitting, by the micro-monitoring system, the human body data information collected by the collection device to the intelligent monitoring system, the method further includes:

detecting whether the micro-monitoring system receives a standby control signal sent by the intelligent monitoring system;

the micro-monitoring system entering a standby state if the detecting indicates that the micro-monitoring system receives the standby control signal;

carrying out the step of transmitting, by the micro-monitoring system, the human body data information collected by the collection device to the intelligent monitoring system if the detecting indicates that the micro-monitoring system does not receive the standby control signal.

Optionally, after the step of processing, by the micro-monitoring system, the human body data information collected by the collection device and transmitting the processed human body data information to a display terminal, the method further includes:

judging whether the collection device continues to collect the human body data information;

carrying out the step of judging, by the micro-monitoring system, whether the intelligent monitoring system is completely started if the judging indicates that the collection device continues to collect the human body data information; and the micro-monitoring system entering the standby state if the judging indicates that the collection device does not continue to collect the human body data information.

Optionally, prior to the step of judging, by the micro-monitoring system, whether the intelligent monitoring system is completely started, the method further includes: initializing the health monitoring system.

The present invention has the following beneficial effects:

the present invention provides a health monitoring system and a data collection method of the health monitoring system. The health monitoring system includes the intelligent monitoring system and the micro-monitoring system, wherein the micro-monitoring system is configured to judge whether the intelligent monitoring system is completely started, and if it judges that the intelligent monitoring system is completely started, then the micro-monitoring system transmits the human body data information collected by the collection device to the intelligent monitoring system; if it judges that the intelligent monitoring system is not completely started, the micro-monitoring system processes the human body data information collected by the collection device and transmits the processed human body data information to the display terminal. The health monitoring system can effectively solve the problem that the intelligent monitoring system fails to monitor the health indicators of the human body during a startup process, and can achieve a real-time monitoring function of the health monitoring system on the human body.

DETAILED DESCRIPTION OF THE EMBODIMENTS

To make those skilled in the art better understand the technical solutions of the present invention, a health monitoring system and a data collection method thereof provided by the present invention will be further described below in detail in combination with the accompanying drawings.

Figure 1:
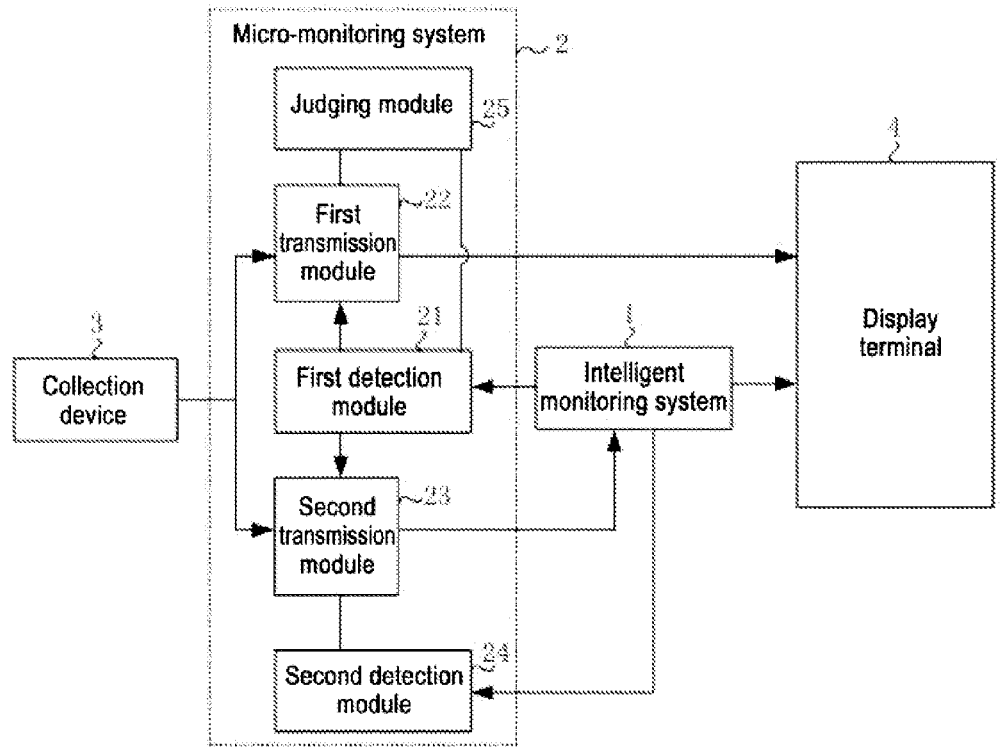
FIG. 1 is a schematic diagram of a structure of a health monitoring system provided by an embodiment of the present invention.

FIG. 1 is a schematic diagram of a structure of a health monitoring system provided by an embodiment of the present invention. As shown in FIG. 1, the health monitoring system includes an intelligent monitoring system 1 and a micro-monitoring system 2, wherein the micro-monitoring system 2 is connected with the intelligent monitoring system 1, and a collection device 3 is connected to the micro-monitoring system 2. The collection device 3 is configured to collect human body data information. The micro-monitoring system 2 is configured to judge whether the intelligent monitoring system 1 is completely started. If the micro-monitoring system 2 judges that the intelligent monitoring system 1 is completely started, the micro-monitoring system 2 transmits the human body data information collected by the collection device 3 to the intelligent monitoring system 1; if the micro-monitoring system 2 judges that the intelligent monitoring system 1 is not completely started, the micro-monitoring system 2 will process the human body data information collected by the collection device 3 and transmits the processed human body data information to a display terminal 4. The display terminal 4 displays according to the processed human body data information in order to provide corresponding health indicators to a monitored object in time.

The collection device 3 may include a plurality of different types of sensors, and by means of different types of sensors, different human body physiological data may be collected. The human body physiological data may be a body temperature value, a blood oxygen value, a blood glucose value, a blood pressure value, a pulse value and the like, and the human body physiological data constitute the human body data information.

The health monitoring system provided by the present invention additionally includes a micro-monitoring system 2 on the basis of the existing intelligent monitoring system 1, and the micro-monitoring system 2 is connected to the collection device 3. The micro-monitoring system 2 is configured to effectively collect, process and display the human body data information when the intelligent monitoring system 1 is in a startup state, so as to effectively monitor the human body in real time.

In the present invention, the difference of the micro-monitoring system 2 and the intelligent monitoring system 1 lies in that, the micro-monitoring system 2 only needs to have simple functions, such as a data transmission function and a data processing function. Therefore, the hardware structure and software structure of the micro-monitoring system 2 are relatively simple, such that the startup speed of the micro-monitoring system 2 is faster and the energy consumption by the micro-monitoring system 2 is lower. When a user starts the health monitoring system, since the startup speed of the micro-monitoring system 2 is faster, the micro-monitoring system 2 may quickly enter a normal working state, while the intelligent monitoring system 1 is in the startup state. In the process that the intelligent monitoring system 1 is in the startup state, the micro-monitoring system 2 may temporarily process the human body data information and transmit the processed human body data information to the display terminal 4, in order to enable the monitored object to understand his/her health indicators in time. Such solution can effectively solve the problem that the health monitoring system in the prior art fails to carry out monitoring when the intelligent monitoring system 1 is in the startup state. After the intelligent monitoring system 1 is completely started, the micro-monitoring system 2 may perform no data processing but transfer the data processing task to the intelligent monitoring system 1 for processing, and meanwhile, the intelligent monitoring system 1 transmits the processed human body data information to the display terminal 4 for display (detailed description will be given below).

It should be noted that, according to a preferable embodiment, the intelligent monitoring system 1 may also be connected to a collection device (not shown in the figure) configured to collect the human body data information. After the intelligent monitoring system 1 is completely started, the micro-monitoring system 2 and the collection device 3 connected to the micro-monitoring system 2 may be in a standby state or a complete halt state, and the intelligent monitoring system 1 performs the monitoring work.

In the present invention, as a preferable solution, the micro-monitoring system 2 further includes a first detection module 21, a first transmission module 22 and a second transmission module 23. The first detection module 21 is connected with the first transmission module 22 and the second transmission module 23, the first detection module 21 is configured to detect whether it receives a complete startup signal sent by the intelligent monitoring system 1; the first transmission module 22 is configured to process the human body data information collected by the collection device 3 and transmitting the processed human body data information to the display terminal 4, when the first detection module 21 detects that the first detection module 21 does not receive the complete startup signal; the second transmission module 23 is configured to transmit the human body data information collected by the collection device 3 to the intelligent monitoring system 1, when the first detection module 21 detects that the first detection module 21 receives the complete startup signal.

In the present invention, the intelligent monitoring system 1 may be correspondingly improved in that, at a time after the intelligent monitoring system 1 is completely started, a complete startup signal can be sent to the micro-monitoring system 2 indicating that the intelligent monitoring system 1 has been completely started. Specifically, when the intelligent monitoring system 1 is in a non-complete startup state, the intelligent monitoring system 1 does not send complete startup signal to the micro-monitoring system 2. Therefore, the first detection module 21 in the micro-monitoring system 2 will judge that the intelligent monitoring system 1 is not completely started if it does not detect the complete startup signal. At this time, the first transmission module 22 in the micro-monitoring system 2 starts working. After the intelligent monitoring system 1 is completely started, the intelligent monitoring system 1 sends a complete startup signal to the micro-monitoring system 2 at a certain time. For example, the intelligent monitoring system 1 may send the complete startup signal immediately after being completely started or with a set time interval. After the first detection module 21 in the micro-monitoring system 2 receives the complete startup signal, the first transmission module 22 in the micro-monitoring system 2 stops working, while the second transmission module 23 in the micro-monitoring system 2 starts working.

In addition, as a preferable solution, the micro-monitoring system 2 may further include a judging module 25, the judging module 25 being connected with the first detection module 21 and the first transmission module 22, and configured to judge whether the collection device 3 continues to collect the human body data information after the first transmission module 22 transmits the processed human body data information to the display terminal 4. When the judging module 25 judges that the collection device 3 continues to collect the human body data information, the first detection module 21 continues to detect whether it receives the complete startup signal sent by the intelligent monitoring system 1; when the judging module 25 judges that the collection device 3 does not continue to collect the human body data information, the micro-monitoring system 2 enters the standby state.

In an example, whenever the first transmission module 22 transmits the processed human body data information to the display terminal 4, the judging module 25 judges whether the collection device 3 continues to collect the human body data information. The judging module 25 may perform the judgment according to the aspiration of a user. Specifically, for example, corresponding judgment buttons of "Continue" and "Not continue" may be arranged on the micro-monitoring system 2. When the user selects the "Continue" button, the judging module 25 judges that the collection device 3 continues to collect the human body data information; when the user selects the "Not continue" button, the judging module 25 judges that the collection device 3 does not continue to collect the human body data information, and at this time, the entire micro-monitoring system 2 enters the standby state.

In addition, as a preferable solution, in the condition that the intelligent monitoring system 1 itself is connected with an independent collection device configured to collect the human body data information, the micro-monitoring system 2 may further include a second detection module 24. The second detection module 24 is connected with the second transmission module 23 and is configured to detect whether the second detection module 24 receives a standby control signal sent by the intelligent monitoring system 1 after the second transmission module 23 transmits the human body data information collected by the collection device 3 to the intelligent monitoring system 1. If the second detection module 24 detects that the second detection module 24 receives the standby control signal, the micro-monitoring system 2 enters the standby state; if the second detection module 24 detects that the second detection module 24 does not receive the standby control signal, the second transmission module 23 continues to transmit the human body data information collected by the collection device 3 to the intelligent monitoring system 1.

Whenever the second transmission module 23 transmits the non-processed human body data information to the intelligent monitoring system 1, the second detection module 24 detects whether the second detection module 24 receives the standby control signal sent by the intelligent monitoring system 1. Specifically, after the intelligent monitoring system 1 sends the complete startup signal to the first detection module 21, the health monitoring system may be in the following working mode: the micro-monitoring system 2 transmits the human body data information collected by the collection device 3 to the intelligent monitoring system 1, and the intelligent monitoring system 1 processes the data and transmits the processed data to the display terminal 4 for display. Alternatively, in the embodiment, since the independent collection device (not shown in the figure) configured to collect the human body data information is further connected to the intelligent monitoring system 1, the intelligent monitoring system 1 may independently achieve monitoring on the human body after being completely started. Due to the relatively complicated above-mentioned working mode wherein the human body data information is collected via the collection device 3 on the micro-monitoring system 2 and data processing is performed by the intelligent monitoring system 1 thereafter, in the embodiment, the intelligent monitoring system 1 will further send standby control information to the micro-monitoring system 2 at a time after sending the complete startup signal to the first detection module 21. After the second detection module 24 in the micro-monitoring system 2 receives the standby control information, the entire micro-monitoring system 2 enters the standby state, and the intelligent monitoring system 1 starts to perform monitoring on the human body independent from the micro-monitoring system 2 via the connected collection device.

As a more specific example, the micro-monitoring system 2 in the present invention is a single chip microcomputer, the single chip microcomputer being connected with the collection device 3 through an I/O interface, and the single chip microcomputer being connected with the intelligent monitoring system 1 through an IIC bus or an SPI bus. It should be known by those skilled in the art that, a corresponding program is written into the single chip microcomputer to enable the single chip microcomputer to achieve the functions of the micro-monitoring system 2 in the embodiment. It should be noted that, the single chip microcomputer in the embodiment may be a single chip microcomputer of MSP 430 series, the working current of the series of single chip microcomputers is only at a μA level when at work, and the standby current can reach an nA level, thus effectively saving the electric energy.

The present invention provides a health monitoring system. The health monitoring system includes the intelligent monitoring system and the micro-monitoring system, wherein the micro-monitoring system is configured to judge whether the intelligent monitoring system is completely started, and if it judges that the intelligent monitoring system is completely started, the micro-monitoring system transmits the human body data information collected by the collection device to the intelligent monitoring system; if it judges that the intelligent monitoring system is not completely started, the micro-monitoring system processes the human body data information collected by the collection device and transmits the processed human body data information to the display terminal. The health monitoring system can effectively solve the problem that the intelligent monitoring system fails to monitor the health indicators of the human body during a startup process, and can achieve a real-time monitoring function of the health monitoring system on the human body.

The embodiment of the present invention further provides a data collection method of the health monitoring system, which is based on the health monitoring system in the embodiment of the present invention.

Figure 2:
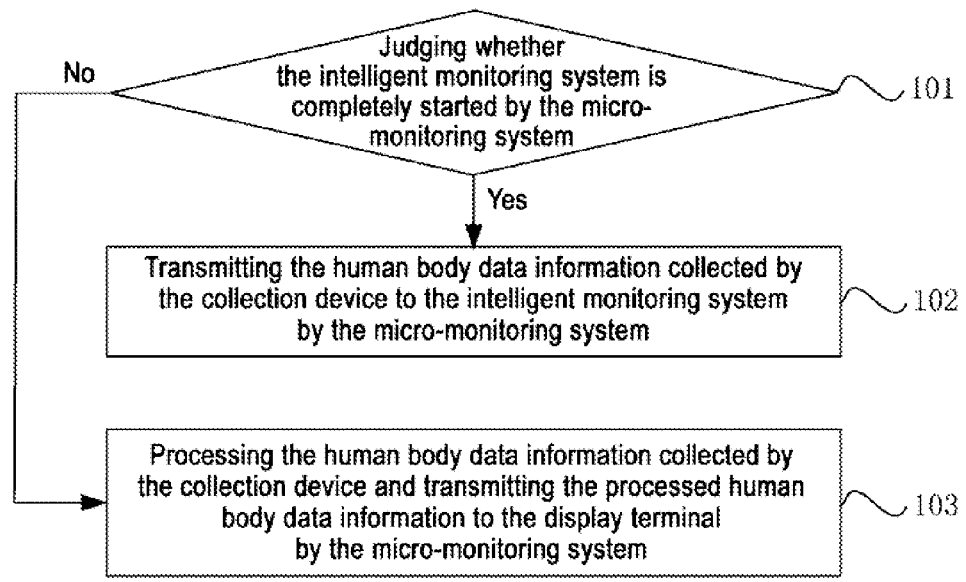
FIG. 2 is a flowchart of a data collection method of a health monitoring system provided by an embodiment of the present invention.

FIG. 2 is a flowchart of a data collection method of a health monitoring system provided by an embodiment of the present invention. As shown in FIG. 2, the method includes:

Step 101: a micro-monitoring system judging whether an intelligent monitoring system is completely started.

Specifically, step 101 includes:

Step 1011: detecting whether the micro-monitoring system receives a complete startup signal sent by the intelligent monitoring system.

In this case, the complete startup signal is a signal sent by the intelligent monitoring system to the micro-monitoring system at a time after the intelligent monitoring system enters a complete startup state and is used for indicating that the intelligent monitoring system enters the complete startup state. If it detects that the micro-monitoring system receives the complete startup signal in step 1011, then in step 101, the micro-monitoring system judges that the intelligent monitoring system is completely started; if it detects that the micro-monitoring system does not receive the complete startup signal in step 1011, then in step 101, the micro-monitoring system judges that the intelligent monitoring system is not completely started.

The step 1011 may be carried out by the first detection module in the above-mentioned embodiment. The description of the first detection module can refer to the description in the above-mentioned embodiment, thus will not be repeated herein.

When it is judged that the intelligent monitoring system is completely started in step 101, the process proceeds to step 102.

Step 102: the micro-monitoring system transmits the human body data information collected by the collection device to the intelligent monitoring system.

Step 102 may be carried out by the second transmission module in the above-mentioned embodiment. Specific reference may be made to the description in the above-mentioned embodiment, thus will not be repeated herein.

When it is judged that the intelligent monitoring system is not completely started in step 101, the process proceeds to step 103.

Step 103: the micro-monitoring system processes the human body data information collected by the collection device and transmits the processed human body data information to a display terminal.

Step 103 may be carried out by the first transmission module in the above-mentioned embodiment. Specific reference can be made to the description in the above-mentioned embodiment, thus will not be repeated herein.

The embodiment of the present invention provides a data collection method of a health monitoring system, which can effectively solve the problem in the prior art that the intelligent monitoring system fails to monitor the health indicators of the human body during the startup process, and can effectively enable the health monitoring system to monitor the health indicators of the human body in real time.

The embodiment of the present invention further provides a data collection method of a health monitoring system, the data collection method is based on the health monitoring system, and the health monitoring system is the health monitoring system in the above-mentioned embodiment.

Figure 3:
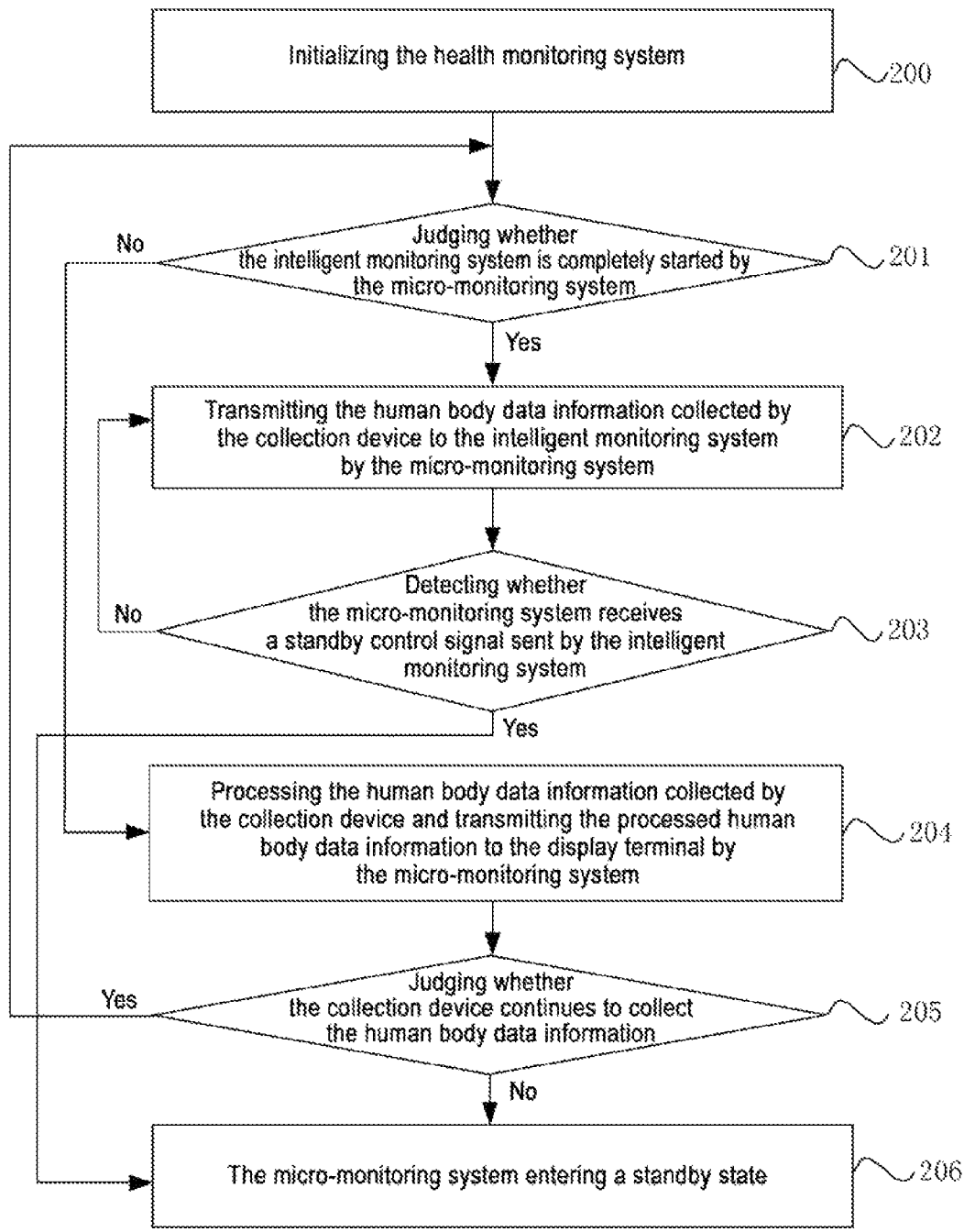
FIG. 3 is a flowchart of a data collection method of a health monitoring system provided by an embodiment of the present invention.

FIG. 3 is a flowchart of a data collection method of a health monitoring system provided by an embodiment of the present invention. As shown in FIG. 3, the method includes:

Step 200: initializing the health monitoring system.

Step 201: a micro-monitoring system judging whether an intelligent monitoring system is completely started.

The step 201 may be carried out by the first detection module in the micro-monitoring system, and the specific process of step 201 is the same as that of step 101 in the above-mentioned embodiment. Specific contents may refer to the description in the above-mentioned embodiment, thus will not be repeated herein.

When it is judged that the intelligent monitoring system is completely started in step 201, the process proceeds to step 202.

Step 202: the micro-monitoring system transmitting the human body data information collected by the collection device to the intelligent monitoring system.

The step 202 may be carried out by the second transmission module in the micro-monitoring system, and the specific process of step 202 is the same as that of step 102 in the above-mentioned embodiment. Specific contents may refer to the description in the above-mentioned embodiment, thus will not be repeated herein.

Step 203: detecting whether the micro-monitoring system receives a standby control signal sent by the intelligent monitoring system.

In the embodiment, the micro-monitoring system further includes a second detection module configured to detect whether the second detection module receives the standby control signal sent by the intelligent monitoring system after the second transmission module transmits the human body data information to the intelligent monitoring system.

If the standby control signal is not detected in step 203, the process will return to step 202; and if the standby control signal is detected in step 203, the process will proceed to step 206.

When it is judged that the intelligent monitoring system is not completely started in step 201, the process proceeds to the following step 204.

Step 204: the micro-monitoring system processing the human body data information collected by the collection device and transmitting the processed human body data information to a display terminal.

The step 204 may be carried out by the first transmission module in the micro-monitoring system, and the specific process of step 204 is the same as that of step 103 in the above-mentioned embodiment. Specific contents may refer to the description in the above-mentioned embodiment, thus will not be repeated herein.

Step 205: judging whether the collection device continues to collect the human body data information.

In the embodiment, the micro-monitoring system further includes a judging module configured to judge whether the collection device continues to collect the human body data information, after the first transmission module transmits the processed human body data information to the display terminal. The specific working process of the judging module can refer to the description in the embodiment, and will not be repeated herein.

When it judges that the collection device continues to collect the human body data information in step 205, the process proceeds to step 201; when it judges that the collection device does not continue to collect the human body data information in step 205, the process proceeds to step 206.

Step 206: the micro-monitoring system entering a standby state.

After the micro-monitoring system enters the standby state, the power consumption of the entire health monitoring system may be effectively reduced so as to save the electric energy.

The embodiment of the present invention provides a data collection method of a health monitoring system, which can effectively solve the problem in the prior art that the intelligent monitoring system fails to monitor the health indicators of the human body in the start process, and can effectively enable the health monitoring system to monitor the health indicators of the human body in real time.

It can be understood that, the foregoing embodiments are merely exemplary embodiments used for illustrating the principle of the present invention. However, the present invention is not limited thereto. Those of ordinary skill in the art may make various variations and improvements without departing from the spirit and essence of the present invention, and these variations and improvements should be contemplated as within the protection scope of the present invention.

The invention claimed is:

1. A health monitoring system, comprising an intelligent monitoring system and a micro-monitoring system, wherein the micro-monitoring system is connected with the intelligent monitoring system, and a collection device is connected to the micro-monitoring system;

wherein the collection device is configured to collect human body data information;

wherein the micro-monitoring system is configured to judge whether the intelligent monitoring system is completely started, and if it judges that the intelligent monitoring system is completely started, the micro-monitoring system transmits the human body data information collected by the collection device to the intelligent monitoring system; if it judges that the intelligent monitoring system is not completely started, the micro-monitoring system processes the human body data information collected by the collection device and transmits the processed human body data information to a display terminal;

wherein the micro-monitoring system comprises a first detection module, a first transmission module and a second transmission module, the first detection module being connected with the first transmission module and the second transmission module;

wherein the first detection module is configured to detect whether the first detection module receives a complete startup signal sent by the intelligent monitoring system;

wherein the first transmission module is configured to process the human body data information collected by the collection device and transmit the processed human body data information to the display terminal, when the first detection module detects that the first detection module does not receive the complete startup signal; and wherein the second transmission module is configured to transmit the human body data information collected by the collection device to the intelligent monitoring system, when the first detection module detects that the first detection module receives the complete startup signal.

2. The health monitoring system of claim 1, wherein the micro-monitoring system further comprises a second detection module, the second detection module being connected with the second transmission module;

wherein the second detection module is configured to detect whether the second detection module receives a standby control signal sent by the intelligent monitoring system, after the second transmission module transmits the human body data information collected by the collection device to the intelligent monitoring system; and wherein if the second detection module detects that the second detection module receives the standby control signal, the micro-monitoring system enters a standby state; and if the second detection module detects that the second detection module does not receive the standby control signal, the second transmission module continues to transmit the human body data information collected by the collection device to the intelligent monitoring system.

3. The health monitoring system of claim 1, wherein the micro-monitoring system further comprises a judging module, the judging module being connected with the first detection module and the first transmission module;

wherein the judging module is configured to judge whether the collection device continues to collect the human body data information, after the first transmission module transmits the processed human body data information to the display terminal; and wherein if the judging module judges that the collection device continues to collect the human body data information, the first detection module continues to detect whether it receives the complete startup signal sent by the intelligent monitoring system; and if the judging module judges that the collection device does not continue to collect the human body data information, the micro-monitoring system enters the standby state.

4. The health monitoring system of claim 1, wherein the micro-monitoring system comprises a single chip microcomputer, the single chip microcomputer being connected with the collection device through an I/O interface, and the single chip microcomputer being connected with the intelligent monitoring system through an IIC bus or an SPI bus.

5. A data collection method of a health monitoring system, wherein the health monitoring system comprises an intelligent monitoring system and a micro-monitoring system, the micro-monitoring system being connected with a collection device, and the method comprises the following steps:

judging, by the micro-monitoring system, whether the intelligent monitoring system is completely started;

transmitting, by the micro-monitoring system, human body data information collected by the collection device to the intelligent monitoring system if the judging indicates that the intelligent monitoring system is completely started;

processing, by the micro-monitoring system, the human body data information collected by the collection device and transmitting the processed human body data information to a display terminal if the judging indicates that the intelligent monitoring system is not completely started;

wherein the step of judging, by the micro-monitoring system, whether the intelligent monitoring system is completely started comprises:

detecting whether the micro-monitoring system receives a complete startup signal sent by the intelligent monitoring system;

judging that the intelligent monitoring system is completely started if the detecting indicates that the micro-monitoring system receives the complete startup signal; and judging that the intelligent monitoring system is not completely started if the detecting indicates that the micro-monitoring system does not receive the complete startup signal.

6. The data collection method of the health monitoring system of claim 5, wherein after the step of transmitting, by the micro-monitoring system, the human body data information collected by the collection device to the intelligent monitoring system, the method further comprises:

detecting whether the micro-monitoring system receives a standby control signal sent by the intelligent monitoring system;

the micro-monitoring system entering a standby state if the detecting indicates that the micro-monitoring system receives the standby control signal; and carrying out the step of transmitting, by the micro-monitoring system, the human body data information collected by the collection device to the intelligent monitoring system if the detecting indicates that the micro-monitoring system does not receive the standby control signal.

7. The data collection method of the health monitoring system of claim 5, wherein after the step of processing, by the micro-monitoring system, the human body data information collected by the collection device and transmitting the processed human body data information to a display terminal, the method further comprises:

judging whether the collection device continues to collect the human body data information;

carrying out the step of judging, by the micro-monitoring system, whether the intelligent monitoring system is completely started if the judging indicates that the collection device continues to collect the human body data information; and the micro-monitoring system entering the standby state if the judging indicates that the collection device does not continue to collect the human body data information.

8. The data collection method of the health monitoring system of claim 5, wherein prior to the step of judging, by the micro-monitoring system, whether the intelligent monitoring system is completely started, the method further comprises: initializing the health monitoring system.

* * * * *